(12) United States Patent
Geismar et al.

(10) Patent No.: US 9,717,848 B2
(45) Date of Patent: Aug. 1, 2017

(54) DATA DERIVED PRE-BOLUS DELIVERY

(71) Applicant: MEDTRONIC MINIMED, INC., Northridge, CA (US)

(72) Inventors: Eric P. Geismar, Encino, CA (US); Francine R. Kaufman, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 297 days.

(21) Appl. No.: 14/603,190

(22) Filed: Jan. 22, 2015

(65) Prior Publication Data

US 2016/0213841 A1 Jul. 28, 2016

(51) Int. Cl.
*A61M 5/168* (2006.01)

(52) U.S. Cl.
CPC .... *A61M 5/16831* (2013.01); *A61M 5/16804* (2013.01); *A61M 2205/50* (2013.01); *A61M 2205/52* (2013.01); *A61M 2205/60* (2013.01)

(58) Field of Classification Search
CPC .......... A61M 5/16831; A61M 5/16804; A61M 2205/60; A61M 2205/52; A61M 2205/50
USPC ......... 604/131, 151, 65, 66, 67; 128/DIG. 1, 128/12, 13
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,814,015 A * | 9/1998 | Gargano ............. A61M 5/1456 604/151 |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |

(Continued)

*Primary Examiner* — Manuel Mendez
(74) *Attorney, Agent, or Firm* — Medtronic MiniMed, Inc.

(57) ABSTRACT

A medical therapy system to deliver a pre-bolus volume of medicant is disclosed. The medical therapy system includes an infusion pump that has a case containing a processor, memory, a drive mechanism, a reservoir, communication hardware and a sensor system. The infusion pump further includes a global positioning system (GPS) receiver to determine GPS coordinates of the infusion pump. The GPS receiver is coupled to the processor that executes stored program instructions to provide notification for confirmation to deliver a pre-bolus volume from the reservoir when the GPS coordinates of the infusion pump are within a specified proximity of GPS coordinates of a saved location.

20 Claims, 6 Drawing Sheets

(56) References Cited

U.S. PATENT DOCUMENTS

| | | |
|---|---|---|
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |

\* cited by examiner

DATA DERIVED PRE-BOLUS DELIVERY

FIELD OF THE INVENTION

This invention relates to infusion systems with and without a sensor to provide feedback regarding a characteristic of a body.

BACKGROUND OF THE INVENTION

Diabetes is a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. To effectively manage the disease, diabetics must closely monitor and manage their blood glucose levels through exercise, diet and medication. In particular, both Type 1 and some Type 2 diabetics rely on insulin delivery to control their diabetes. Traditionally, insulin has been injected with a syringe multiple times during the day, usually self-administered by the diabetic. In recent years, use of continuous subcutaneous insulin infusion therapy has been increasing. This therapy delivers insulin to diabetics using devices worn on a belt, in a pocket, or the like, with the insulin delivered from a reservoir via a catheter with a percutaneous needle or cannula placed in the subcutaneous tissue.

External infusion devices allow Type 1 and Type 2 diabetics to better manage and control their diabetes. The external infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and overnight. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device. Exemplary devices are described in U.S. Pat. No. 6,554,798 issued on Apr. 29, 2003 to Mann et al., and entitled "External Infusion Device with Remote Programming, Bolus Estimator and/or Vibration Alarm Capabilities," which is specifically incorporated by reference herein.

Delivering a pre-bolus volume of insulin before eating a meal can decrease the total amount of insulin delivered to compensate for the consumption of foods and drinks. Automating or partially automating programming for the infusion device can help simplify and improve therapy. Knowing a user's location can enable partial or full automation of specific aspects of infusion device therapy including the delivery of a pre-bolus. Accordingly, it can be beneficial to include GPS receiver data as part of infusion therapy.

SUMMARY OF THE DISCLOSURE

In one embodiment a medical therapy system to deliver a pre-bolus volume of medicant is disclosed. The medical therapy system includes an infusion pump that has a case containing a processor, memory, a drive mechanism, a reservoir, communication hardware and a sensor system. The infusion pump further includes a global positioning system (GPS) receiver to determine GPS coordinates of the infusion pump. The GPS receiver is coupled to the processor that executes stored program instructions to provide notification for confirmation to deliver a pre-bolus volume from the reservoir when the GPS coordinates of the infusion pump are within a specified proximity of GPS coordinates of a saved location.

In another embodiment the medical therapy system to deliver a pre-bolus volume of medicant includes an infusion pump that has a case containing a processor, memory, a drive mechanism, a reservoir and communications hardware. The medical therapy system further includes a global positioning system (GPS) receiver to determine GPS coordinates of the infusion pump. The GPS receiver provides GPS coordinates to the processor that further executes stored program instructions to request confirmation to deliver a pre-bolus volume from the reservoir when the GPS coordinates of the infusion pump are within a specified proximity of GPS coordinates of a known location.

In still other embodiments a medical therapy system to deliver a pre-bolus of medicant includes an infusion pump having a case that contains a processor, memory, a drive mechanism, a reservoir and communication hardware. The medical therapy system further includes a controller having a case that contains a controller processor, controller memory and controller communication hardware that controls the infusion pump. In one embodiment a GPS receiver is included with the controller and provides GPS data to the processor and the controller processor. In still another embodiment a GPS receiver is found in both the controller and the infusion pump and each supplies GPS data to the respective processor. In yet a further embodiment, the communication hardware in both the controller and the infusion pump receives GPS data from a separate device. The GPS data includes GPS coordinates to determine a location of the infusion pump and controller enabling delivery of a pre-bolus volume from the reservoir when the GPS coordinates of the infusion pump are within a specified proximity of GPS coordinates of a known location.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION

Figure 1:
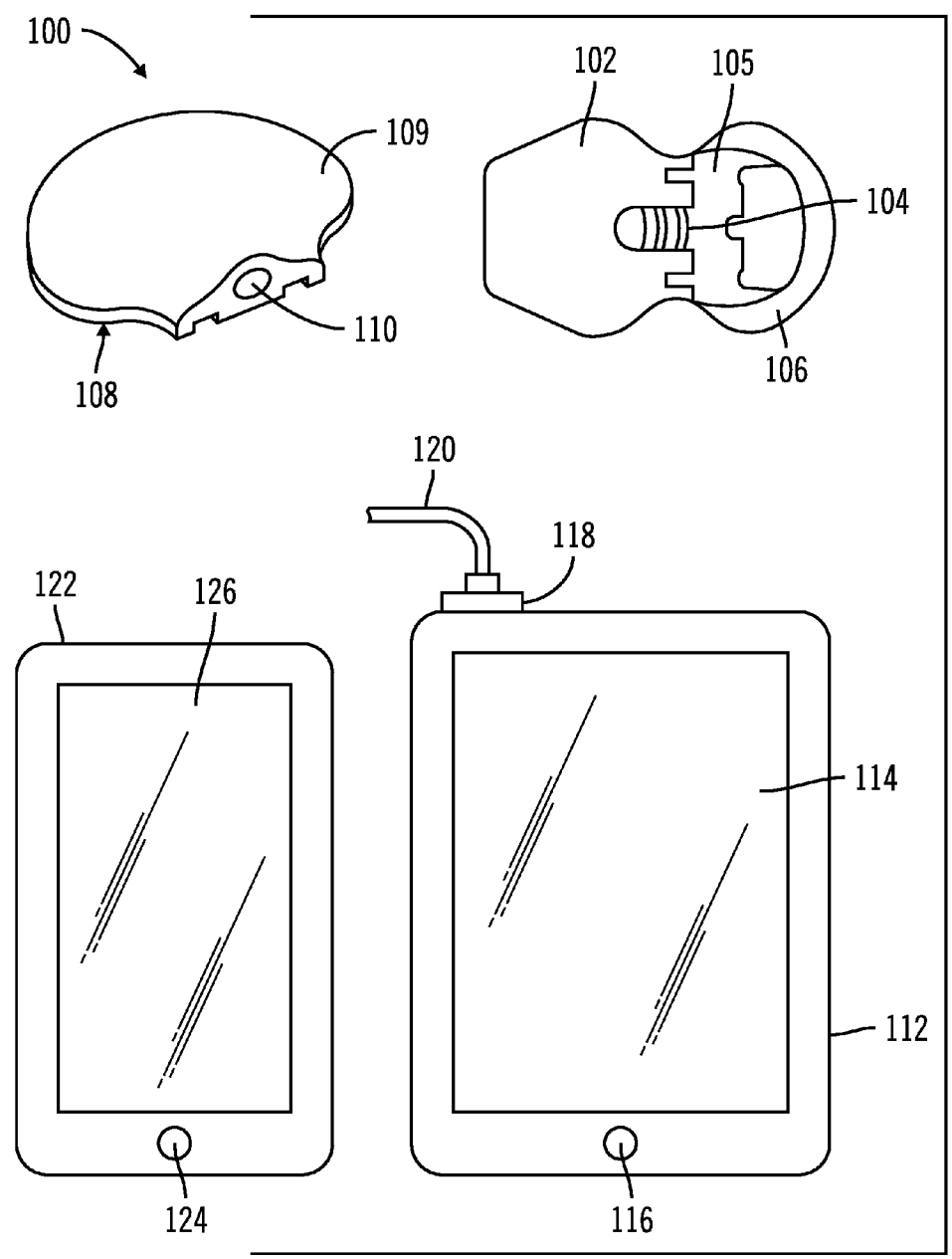
FIG. 1 is an exemplary illustration of components within an infusion system.

As shown in the drawings for purposes of illustration, the invention is embodied as a portable infusion system with an optional sensor set that provides continuous data of the sensor readings to the infusion system. In some embodiments a wireless controller having a touchscreen user interface and integrated GPS receiver is used to control an infusion pump having minimal or no user interface. In other embodiments, the infusion pump itself includes a GPS receiver and a touchscreen user interface. In still other embodiments both a wireless controller and an infusion pump include a GPS receiver and a user interface. In yet another embodiment, the infusion pump or controller receives GPS data from a third device that is separate from the infusion system. In such an embodiment receiving GPS data from another device enables GPS functionality without having a GPS radio natively integrated with the infusion system. In every embodiment, enabling the GPS receiver allows the infusion pump to deliver a pre-bolus amount of fluid based solely or partially on the location of the user.

The term "pre-bolus" is used to describe an infusion volume delivered to a user prior to the delivery of a larger bolus. In embodiments dealing with the diabetes therapy, the pre-bolus introduces a small amount of insulin in anticipation of consumption of carbohydrates. The benefit of the pre-bolus is the insulin introduced before consuming carbohydrates has a greater effect on blood glucose values over time than if the same volume of insulin was introduced after consuming carbohydrates. The pre-bolus can be further distinguished from a bolus typically delivered with a meal in that the pre-bolus does not necessarily need to be tailored to specific amounts of carbohydrates being consumed. For example, in some embodiments a pre-bolus volume is set at 0.25 units while a meal bolus is typically customized based on the consumed carbohydrates. In other embodiments, the pre-bolus volume can vary based on the time of day to accommodate when a user eats larger meals. Generally, in most embodiments the pre-bolus will be a small volume of insulin between 0.1 and 5 units of insulin.

Because commercial GPS provides a "worst case" pseudo-range accuracy of 7.8 meters at a 95% confidence level, some embodiments of the GPS enabled infusion system may request user confirmation before delivery a pre-bolus. In other embodiments, pre-bolus delivery is performed automatically based on a number of threshold criteria being fulfilled. For some infusion therapies, such as but not limited to infusing insulin for diabetes therapy, a pre-bolus delivered before ingesting a meal can reduce the amount of bolus insulin required to offset consumed carbohydrates. A GPS enabled infusion system can be used to help determine if a user is within an area where many restaurants are located or even actually within a restaurant. Based only on GPS enabled location data the user may be requested to acknowledge whether a pre-bolus infusion is delivered. In other embodiments additional data supplements location data to minimize the likelihood of an unwanted notification regarding a pre-bolus delivery. In some embodiments the infusion system indicates initiation of pre-bolus delivery via a user configurable audible or vibration notification. This notification provides the user the option to cancel the delivery in the off chance a pre-bolus was accidentally programmed.

Additionally, the term "restaurant" or "café" as used throughout this document should be construed broadly to encompass locations that provide food and/or beverages whose consumption would result in a bolus being delivered for diabetes therapy. While some specific types of restaurants may be discussed regarding particular embodiments, the generic term restaurant is intended to encompass everything from the humble roadside lemonade stand, street vendor cart or soup kitchen to restaurants rated in the MICHELIN GUIDE. For purposes of this disclosure, it should be noted that a user's home could be considered a "restaurant" or "café" if their home is where boluses are commonly delivered.

In embodiments of the present invention, the analyte sensor set and infusion system determine glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV or Hepatitis C), or the like. In other embodiments, the infusion system may also include the capability to be programmed to record optional sensor data at specified time intervals. The infusion system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, subdermal sensors, skin surface sensors, or the like. Embodiments may measure and record sensor readings on an intermittent or continuous basis.

FIG. 1 is an exemplary illustration of components within an infusion system 100, in accordance with embodiments of the present invention. The sensor 102 is shown from an exemplary top view as if it has been inserted into a patient. In one embodiment the sensor 102 utilizes an electrode-type sensor while in alternative embodiments, the sensor 102 may use other types of sensors, such as chemical based, optical based or the like. In further alternate embodiments, the sensor 102 may be of a type that is used on the external surface of the skin or placed below the skin layer of the user or placed in the blood stream of the user. Other embodiments of a surface mounted sensor can utilize interstitial fluid harvested from the skin.

In some embodiments, the sensor 102 is an assembly commonly known as a "sensor set" that includes, but it not limited to the connector 104, sensor adhesive (not shown) covered by an adhesive backing 106, an introducer needle (not shown in FIG. 1), a sensing portion of the sensor to be placed in a body (not shown), and a mounting base 105. In one embodiment the connector 104 is integrally injection molded from plastic with the mounting base 105. The connector 104 further includes electrical contacts that interface with contacts on the sensor. On a side opposite that is shown in FIG. 1, the adhesive is applied to the mounting base 105 and the adhesive backing 116 is further applied over the adhesive.

An electronic package 108 is also included in the infusion system 100. The electronics package 108 includes a package housing 109 with a package port 110. The package port 110 is designed to couple with the electrical contact on the connector 104 thereby providing power and other electrical interfaces between the electronics package 108 and the sensor 102. In one embodiment the electronics package further includes a power source, processor and transmitter within the package housing 109. The power source provides power for the processor and transmitter and additionally powers the sensor 102 when coupled to the connector 104. In such an embodiment, signals generated by an installed sensor can be processed via the processor and transmitted to another device such as, but not limited to, infusion pump 112 and/or controller 122. In other embodiments, the electronics package 108 includes at least a power source, processor, transmitter along with memory and a receiver. In these embodiments sensor signals from an installed sensor are stored to memory within the package housing 109 and periodically transmitted to the infusion pump 112 or other devices configured to communicate with the electronics package 108. Additionally, the inclusion of the receiver within the electronics package 108 would enable two-way communication between other devices and the electronics package 108.

The inclusion of memory within the electronics package 108 enables the combined electronics package 108 and sensor 102 to be used as a Holter-type recording device that uses the package port 110 to interface with either the sensor 102 or a docking station (not shown) that is further connected to a computer of tablet computing device. When used as a recording device the combined electronics package 108 and sensor 102 have the capability to record and store data as it is received from the sensor 102. When the electronics package 108 is coupled to a docking station the data stored on the memory of the electronics package 108 can be transferred to networked or local data storage and analyzed using general computing processors such as desktops, laptops, notebooks, netbooks, or handheld computing devices such as, but not limited to smart phones, tablets and the like. To enable data transfer through the dock, the dock may further include a data transfer cable such as, but not limited to USB, Thunderbolt or Ethernet directly coupled to a computing device.

The infusion pump 112 included in the infusion system 100 includes a tubing 120 that is in connected to a reservoir 118 within the infusion pump 112. Other characteristics of the infusion pump include a display 114 and a user interface 116. In some embodiments the display 114 is a touchscreen thereby making the display 114 an integrated component of the user interface 116. The infusion pump 112 can further include a radio transmitter and receiver that enables wireless communication. In some embodiments the radio transmitter is a BLUETOOTH radio that includes the BLUETOOTH LOW ENERGY profile. In other embodiments a custom secure radio transmission system or protocol is used. The radio transmitter within the infusion pump 112 enables wireless transmission with the electronics package 108 thereby allowing sensor data to be processed and analyzed by the infusion pump 112 along with showing sensor data on the display 114. In some embodiments there are multiple radio transmitters within the infusion pump 112 some of which are capable of transmitting and receiving data using at least one of the commercially available standards such as, but not limited to Long Term Evolution (LTE), GPRS, EDGE, EVDO, Wi-Fi, WiGig and the like.

In some embodiments a controller 122 having a controller display 126 and controller interface 124 is optional. In other embodiments the controller 122 may be required. An example of an embodiment where the controller 122 may be required is a system where the infusion pump 112 does not include a user interface or has a minimal or simplified user interface, such as but not limited to patch pump systems. In all embodiments, the controller display 126 can be a touchscreen enabling the controller display 126 and the controller interface 124 to function as a user interface to remotely control the infusion pump 112. The controller 122 includes a controller radio (not shown) that enables bi-directional communication between the controller 122 and the infusion pump 112. In some embodiments the controller radio uses the BLUETOOTH LOW ENERGY communication protocol to communicate with the infusion pump 112. In other embodiments a proprietary secure communication protocol is used between the controller 122 and the infusion pump 112. The controller radio can further enable communication between the controller 122 and the electronics package 108 associated with the sensor set. In one embodiment the controller 122 is a commercially available mobile phone configured to run proprietary or customized software capable of controlling the infusion pump 112. In other embodiments the controller 122 is a custom device specifically designed to control the infusion pump 112.

Transmission of sensor data to the infusion pump 112 further enables real-time glucose monitoring which can further enable enhanced insulin infusion control, such as, but not limited to low-glucose suspend functionality. In these embodiments if the sensor data indicates a blood sugar level below a specified threshold, the infusion pump 112 can suspend delivery of basal insulin. In other embodiments, the infusion pump 112 or the controller 122 can process sensor data and automatically make therapy changes such as basal rates, bolus suggestions and the like. The examples provided are intended to be exemplary and should not be construed as limiting; other aspects of continuous subcutaneous insulin infusion can be automatically modified based on sensor data. In some embodiments the raw sensor data measured by the sensor 102 is manipulated or processed using the processor within the electronics package 108 to determine sensor data from interstitial fluid that corresponds to a blood glucose level. In still other embodiments, the electronics package 108 transmits the raw sensor data to the insulin pump 112 where the raw sensor data is processed to correspond to a blood glucose level. In still other embodiments, the electronics package 108 transmits both the raw sensor data and a first calculated blood glucose level to the insulin pump. In these embodiments the insulin pump can then use a different algorithm to calculate a second blood glucose level from the raw sensor data. The second blood glucose level then being used in conjunction with the first blood glucose level to determine a third calculated blood glucose level.

Further description regarding the sensor and associated sensor set can be found in U.S. Pat. No. 6,248,067, entitled ANALYTE SENSOR AND HOLIER-TYPE MONITOR SYSTEM AND METHOD OF USING THE SAME, U.S. Pat. No. 5,586,553, entitled TRANSCUTANEOUS SENSOR INSERTION SET, and U.S. Pat. No. 5,594,643, entitled DISPOSABLE SENSOR INSERTION ASSEMBLY, all of which is herein incorporated by reference.

Figure 2A:
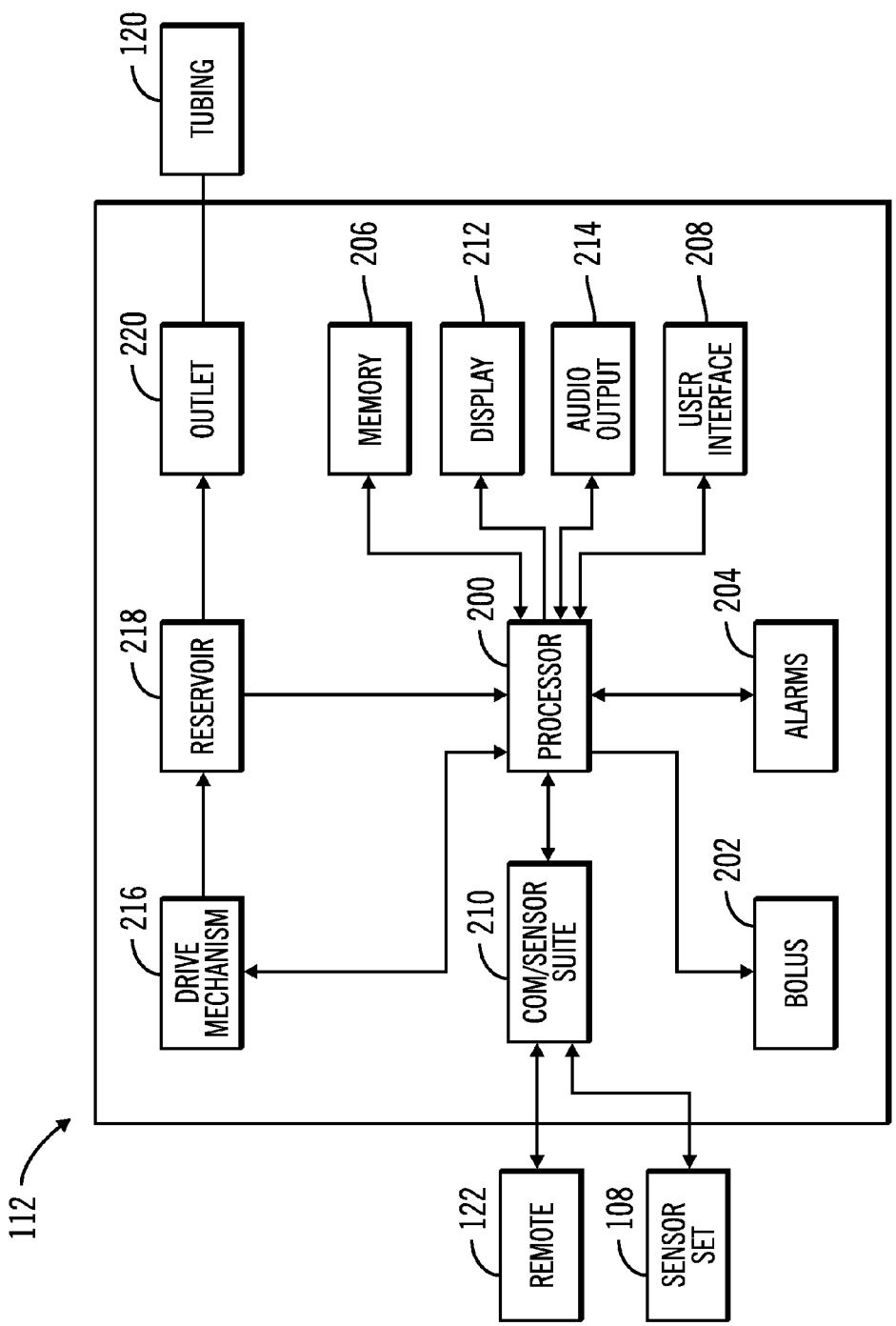
FIGS. 2A and 2B are block diagrams illustrating exemplary components within the infusion pump and the controller.
Figure 2B:
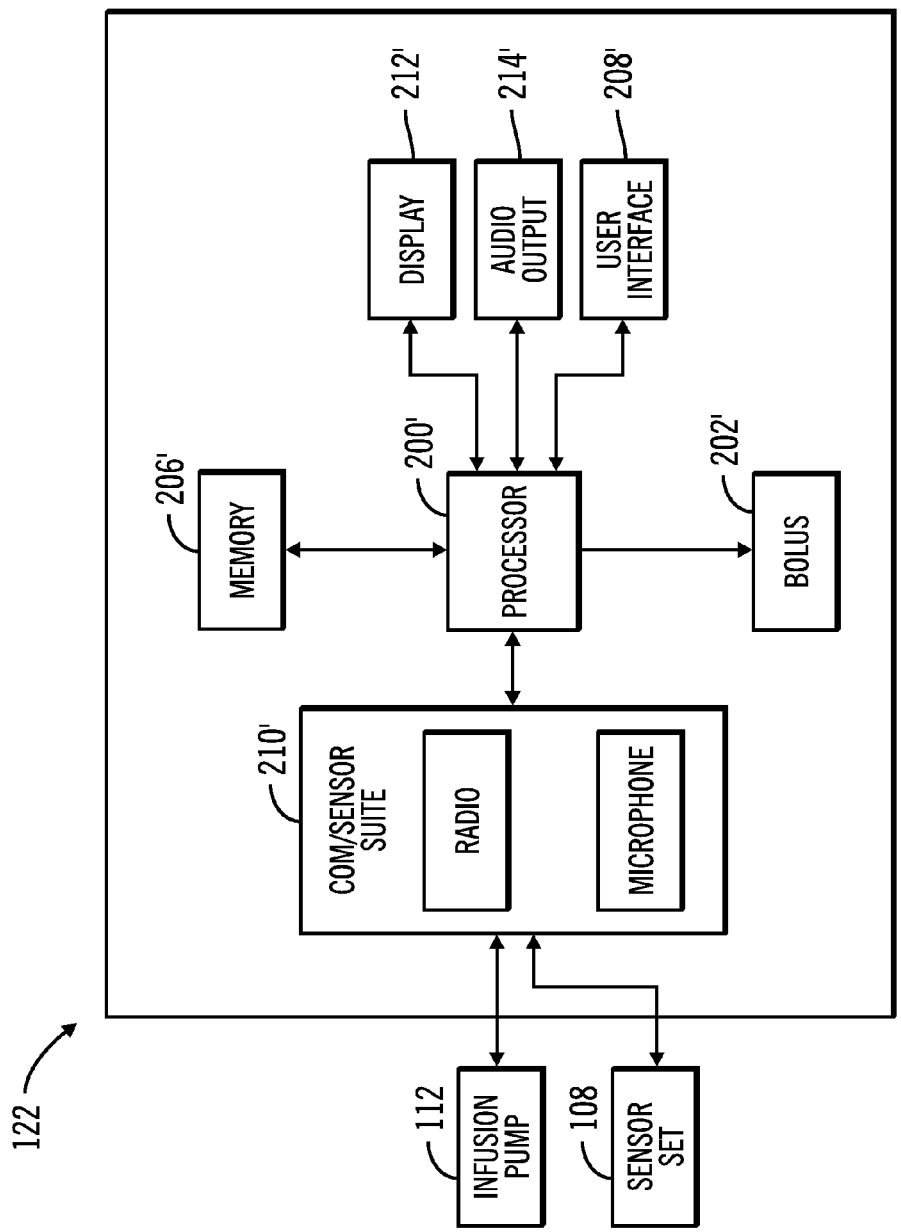

FIGS. 2A and 2B are block diagrams illustrating exemplary components within the infusion pump 112 and the controller 122, in accordance with embodiments of the present invention. The components or elements included in FIGS. 2A and 2B are intended to be illustrative of selected components and should not be construed as inclusive of all components within the infusion pump and controller. As illustrated in FIGS. 2A and 2B the infusion pump and controller share many common components. This is not be construed as the infusion pump and controller having identical components with identical part numbers. Rather, for simplicity, controller components that have analogue in the infusion pump will be designated with a "prime". These components are intended to perform similar, identical or redundant functions in the controller as the analogous part in the infusion pump. For example, the infusion pump 112 includes a processor 200 capable of executing program instructions that are stored in either memory integrated within the processor 200 or in a memory 206. Likewise, the controller 122 includes a processor 200' and a memory 206' that performs many, but not all of the same functions as the processor 200 and memory 206 in the infusion pump 112.

The program instructions executed by the processor 200 enable actuation of a drive mechanism 216 that is coupled to the processor. The drive mechanism 216 is further coupled to a reservoir 218 that contains a fluid to be infused into a user via outlet 220 and tubing 120. The infusion pump 112 further contains bolus functions as illustrated by bolus element 202 coupled with processor 200. Bolus element 202 can enable various types and profiles of bolus delivery from the infusion system 112. In some embodiments the bolus element 202 is optionally found in the controller 122 as bolus element 202'.

Further coupled to the processors 200/200' are an alarms component 204/204', a display 212/212', audio output 214/214' and a user interface 208/208'. Accessible via the user interface 208/208' and display 212/212', the alarms component 205/205' allows users to program various alarms conditions such as, but not limited to low or high level thresholds for sensor measurements, periodic alarms and the like. The alarms component 205/205' can use the display 212/212' and audio output 214/214' to draw the attention of a user regarding an alarm condition. In some embodiments the alarm component 205/205' further includes a vibration alarm that enables vibration of the entire infusion pump 112, controller 122 or both so a user can be discretely notified of an alarm condition without the use of audio output 214/214'. In one embodiment audio output 214/214' in accomplished via a speaker within the case of the infusion pump. In other embodiments, a piezoelectric sound generator can be used to generate audio output 214/214'. Audio output 214/214' along with vibration functions of alarm component 205/205' can be used to notify a user of an alarm condition and also to provide audio and/or tactile feedback regarding operation of the user interface.

The display 212/212' can show various information regarding the status of the infusion pump 112, the controller 122, both and/or an associated sensor, or the measurements from the sensor itself. Examples of infusion pump 112, controller 122 or sensor status that can be shown on the display 212/212' include, but are not limited to battery life, volume of fluid in the reservoir, connection status with the sensor, remaining sensor life, sensor hydration levels, sensor readiness and the like. The display 212/212' also displays real-time data from the sensor along with trend data based on sensor readings and user specified threshold values stored in the memory 206/206'. Via the user interface 208/208', the display 212/212' can be configured by a user to display particular information in a particular format. For example, in one embodiment the user can choose to have sensor data displayed as a moving line graph with a user defined number of previous samples used to determine trend data. In another embodiment, sensor data can be displayed as a bar graph or other graphical format. Other embodiments allow users to define fonts, font sizes, kerning, date format, clock format/size and the like.

The processor 200/200' within the infusion pump 112 or the controller 122 is further coupled to a communications and environmental sensor suite 210/210'. Within the communication and environmental sensor suite 210/210' are radios to enable secure wireless communications and environmental sensors such as, but not limited to accelerometers, ambient light sensors, global positioning satellite (GPS) receivers, microphones, clocks, compasses and even cameras. The radios within the infusion pump 112 and controller 122 enable communication between the infusion pump 112, the controller 122 and the electronics package 108 associated with the sensor set. In some embodiments the radios within the infusion pump 112 enable communication with additional devices other than those within the infusion system. This enables the infusion pump 112 to receive GPS data from devices such as, but not limited to mobile phones, watches, standalone GPS navigation devices, GPS navigation system integrated within automobiles and the like. In some embodiments wireless transmission of GPS data is performed using the BLUETOOTH standard thereby enabling GPS capability for an infusion system that may not include an integrated GPS receiver.

The environmental sensors provide data to the processor within the infusion pump or controller regarding particular physical characteristics or environmental conditions around the infusion system. For example, inclusion of accelerometers enables the processor to determine the orientation of the infusion pump thereby automatically orienting pump information on the display to be easily readable by the user. Similarly ambient light sensors can enable the display to be brightened or dimmed automatically. Likewise, a microphone may detect ambient noise and automatically adjust audible alarms to appropriate levels. In other embodiments the microphone is utilized to enable voice recognition to program in order to interact with the infusion pump. Some examples of using voice recognition to interact with the infusion system include, but are not limited to confirming delivery of a pre-bolus from the reservoir, initiating and programming a bolus or pre-bolus, and modifying a suggested bolus or pre-bolus. In other embodiments, data combinations from various sensors such clocks, ambient light sensors and microphones can be used to automatically determine audible alarm intensity. For example, if a clock indicates it is 3 AM, the ambient sensors determine it is dark, microphones detect very little ambient noise, and accelerometers indicate sporadic movement it may be determined the user is asleep and audible alarms may be automatically programmed to start off somewhat quietly and gradually increase in intensity over time.

Embodiments that include a camera further enable the use of QR or similar barcodes to enable delivery of pre-bolus volumes. For example, a user could use a camera to take a picture of a barcode or QR code thereby enabling correlation to the nutritional information of the product thereby simplifying calculation of a pre-bolus. In some embodiments, integration of a camera within the infusion system is optional. In these embodiments, a separate wireless device such as, but not limited to, a mobile phone or wireless communication enabled camera captures barcodes or QR codes and wirelessly transmits the nutritional value associated with the product to the controller or the infusion pump within the infusion system.

In embodiments having a GPS receiver, the GPS signal determining the location of a user alone can be used to initiate a pre-bolus program routine. In other embodiments a pre-bolus delivery program routine can be initiated based on the location as determined by the GPS receiver in combination with other data such as, but not limited to data from the environmental sensors, an internal clock or even past infusion delivery data. Due to geographic, architectural or physical limitation it may be necessary to use an amplified or active indoor/outdoor GPS antenna or repeater to ensure a GPS signal can be received by the insulin delivery system. The use of GPS as an acronym for Global Positioning System should not be construed as limiting the disclosure to receivers using signals from GPS satellites. Other satellite based positioning/navigation systems such as, but not limited to GLONASS, Galileo, Beidou, COMPASS, IRNSS, and QZSS should be considered to fall within the scope of this disclosure. Additionally, while GPS signals may be used to determine a location of a user other techniques such as, but not limited to databases correlating Wi-Fi signals to locations can also be used. In one embodiment Wi-Fi signals are used to supplement GPS signal data to provide enhanced location resolution in urban areas. In still other embodiments, Wi-Fi signals alone are used to determine the location of a user.

Figure 3:
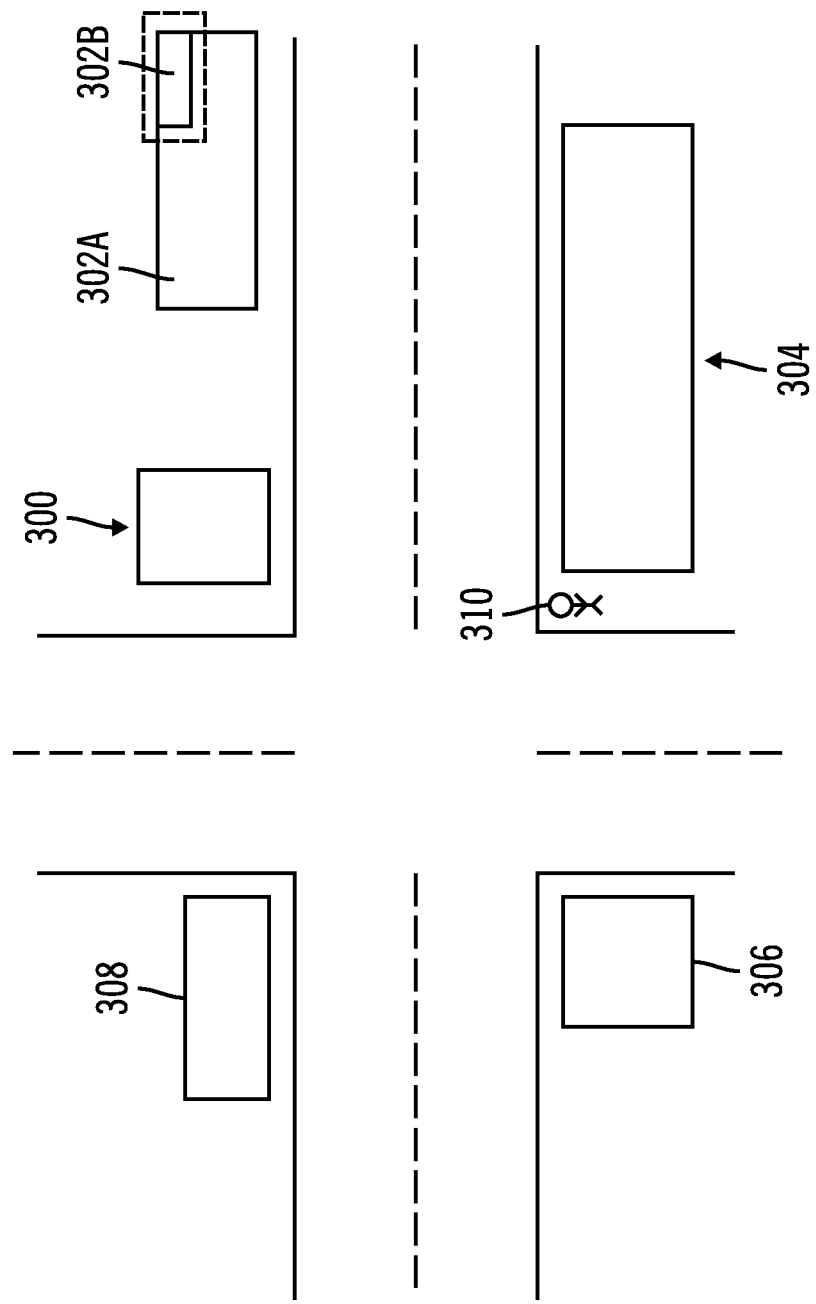
FIG. 3 is an exemplary illustration of a location where GPS receiver data with or without supplemental data is used to determine if a user receives notification of a pre-bolus.

FIG. 3 is an exemplary illustration of a location where GPS receiver data with or without supplemental data is used to determine if a user receives notification of a pre-bolus, in accordance with embodiments of the present invention. FIG. 3 illustrates various buildings 300, 302A, 304, 306 and 308 where a GPS enabled infusion device carried by user 310 provides automatic or user confirmed pre-bolus delivery. In one embodiment building 302A includes a café 302B such as, but not limited to a DUNKIN DONUTS or STAR-BUCKS. Accordingly, upon GPS data indicating the user 310 is within the café 302B the infusion pump can be programmed to prompt or notify the user for confirmation to deliver a pre-bolus volume in anticipation of carbohydrate consumption. In some embodiments without confirmation within a specified period of time, the pre-bolus is automatically canceled. In other embodiments, without confirmation within a specified period of time, the pre-bolus is automatically delivered. Regardless of whether the pre-bolus is automatically cancelled or delivered, in both embodiments the specified period of time can be configured.

In other embodiments, a user can program the infusion device to correlate specific GPS coordinates with a restaurant/café/bistro or the like. For example, the user 310 can program the infusion system to recognize the GPS coordinates for building 300 as a restaurant. In some embodiments the user interface of the infusion system allows entry of GPS coordinates to reference as pre-bolus locations. In other embodiments third party applications such as, but not limited to GOOGLE MAPS, BING MAPS, or the like can be used to upload GPS coordinates for restaurant locations to the infusion system. In still other embodiments when a user delivers a bolus or pre-bolus the infusion system can automatically record into memory the time, bolus volume and GPS coordinates when the infusion was delivered. In further embodiments, when a bolus is delivered a user can be prompted on either the infusion device or controller to save the current GPS coordinates into memory, or geo-tagged the current location as a restaurant for future pre-bolus prompting. In addition to automatically or manually geo-tagging bolus locations, embodiments that include a Wi-Fi radio can further record or log available Wi-Fi signals and relative Wi-Fi signal strengths with GPS coordinates to further refine the location of a user. Thus, a GPS enabled infusion system can be programmed with a user's favorite restaurants in order to prompt the user regarding pre-bolus delivery on future visits.

For example, GPS coordinates for a restaurant 304 have been recorded or programmed into the memory of the infusion system in order to better tailor a user's therapy based on their environment. In embodiments where the infusion system is used to deliver insulin for diabetes therapy a user automatically receive notification that a pre-bolus infusion may be beneficial when they are within close proximity of the GPS coordinates for the restaurant 304. In another embodiment, if a user remains in close proximity to the GPS coordinates of the restaurant 304 for a threshold period of time, a suggested pre-bolus will automatically be delivered unless canceled by the user. In other embodiments the user has the option to modify the suggested bolus. In still other embodiments, the suggested or modified pre-bolus is not delivered without confirmation from the user. Various methods can be used to accept, modify or cancel delivery of a pre-bolus. In many embodiments the user interface for either the infusion pump or controller is used. In embodiments utilizing voice recognition, a user can speak commands that are detected by the microphone within the infusion system.

All of the different embodiments are able to monitor movement of the user within specified periods of time to estimate when the user is seated or waiting for a table in a restaurant. For example, accelerometer data can be used to supplement GPS data to determine if a user is walking or running. In some embodiments the threshold period of time a user remains within the proximity of known GPS coordinates is automatically set to somewhere between five and thirty minutes. In other embodiments the threshold time by default is set to somewhere between ten and fifteen minutes. In still other embodiments, the time threshold is user configurable including very short durations of time measured in seconds.

To accommodate instances where a restaurant has a waiting time before the user would be seated, some embodiments include a delay or snooze function before the pre-bolus is delivered. Thus, upon entering proximity of specified GPS coordinates a user is prompted regarding delivery of a pre-bolus. To accommodate an expected wait time before being seated a user has the option to snooze the pre-bolus delivery for a specified period of time. The actual snooze period of time is either user defined or preset. Upon the snooze time elapsing, the user is prompted regarding delivery of a pre-bolus. The user has the option to further snooze/delay the delivery of the pre-bolus, cancel the pre-bolus or proceed with programming or delivery of a suggested pre-bolus. Thus, the GPS enabled infusion system entering the proximity of specified GPS coordinates enables the infusion pump to automatically, or request user confirmation to, deliver a pre-bolus infusion.

In other embodiments, a user is prompted regarding delivery of a pre-bolus when they enter an area with a relatively high density of restaurants. These embodiments can assist a user deliver a pre-bolus when they are traveling outside of the area they frequent such as when they go on vacation. In these embodiments GPS coordinates reported by the GPS receiver are compared to GPS coordinates for known restaurants as cataloged by third-party commercial services such as, but not limited to GOOGLE MAPS, YELP!, or ZAGAT. To avoid over alerting or excessive notifications, a user can define a threshold number of restaurant, or restaurant density within their proximity before prompting the user to deliver a pre-bolus. Additionally, some embodiments further include exceeding a time threshold within the area exceeding the threshold number of restaurants before notification of a pre-bolus is given to a user.

In particular embodiments a user has the option of enabling or disabling pre-bolus prompts based on restaurant density as a setting of the pre-bolus feature of the infusion system. In one embodiment the infusion system includes a pre-bolus menu item named "travel" or "explorer" mode that can be toggled on or off by a user. In one embodiment once travel/explorer mode is toggled to on, a user can further configure the threshold number of restaurants and/or time within the proximity of the restaurants. In additional embodiments, a user is further allowed to select the types of restaurants that are included within the threshold number. For example, the user is allowed to choose whether to include fast-food chains, café s, coffee shops, casual dining and the like. In embodiments using commercial indices, additional criteria can be filtered such as, but not limited to cost, review classification (such as "stars", "likes", or "thumbs-up"). Thus, only when the threshold value for user defined preferred selection of restaurants is fulfilled will the infusion system prompt the user regarding pre-bolus delivery.

Supplying too many notifications can become intrusive and lead a user to disable a feature. Accordingly, GPS data can be supplemented by additional data to further improve usability of the pre-bolus feature within the infusion system. With many embodiments, data from previous bolus deliveries is examined to determine trends associated with time, volume and location in an effort to provide pre-bolus notifications that are meaningful and impactful. For example, analyzing time data from previous bolus deliveries associated with meals can determine when a user normally eats their meals. The time data regarding meals enables the infusion system to optimize when GPS data is monitored. In some embodiments the GPS receiver can be operated in a lower power consumption mode when outside of the specific and optimized GPS data monitoring time. This can be very beneficial for portable infusions systems to maximize usage before changing or recharging a battery.

In some embodiments the GPS location data is processed and a pre-bolus notification is provided to the user only if the time of day is within a defined period of when the user delivers a bolus consistently associated with a meal. For example, if a user consistently delivers a bolus around noon, the defined period to process GPS data analysis for pre-bolus recommendations is one hour before noon, or 11 AM. In other embodiments the defined period to process GPS data is user configurable. Thus, someone with a relatively open schedule can set the defined period to process GPS data in order to accommodate their needs. Likewise an individual with a regimented schedule could restrict the defined period to analyze GPS data to a very narrow window in order to avoid over intrusive pre-bolus notifications. To accommodate meals or snacks that fall outside of regular schedule many embodiments allow a user to manually initiate a pre-bolus volume via the user interface or voice recognition.

Bolus volume trends can be analyzed much like bolus times in order to provide the user a suggested pre-bolus volume. In some embodiments, when a pre-bolus prompt is provided to the user a suggested volume of the pre-bolus is included. The suggested pre-bolus volume can be customized not only based on previous pre-bolus volumes, but also on GPS location data. Thus, a pre-bolus suggested for a restaurant where a user consistently eats a salad could be necessarily different than a pre-bolus suggested for a restaurant where the user consistently eats pasta.

Another feature enabled by an integrated GPS receiver is integrating GPS coordinates with restaurant or café locations to enable users to easily access nutritional information on either the controller or the infusion pump. Enabling GPS location reporting allows a dialog box or notification to be made on the display that enables the user to access nutritional information specific to the establishment they entered or they are near. In some embodiments, accessed nutritional information can be used to determine a pre-bolus recommendation if previous bolus data is not available for a given location. This enables a pre-bolus recommendation that takes into account the general type of establishment be it an ice cream shop or a juice bar. In some embodiments a pre-bolus volume can be determined when the user selects items they wish to order from a graphical display of icons or a simple list that corresponds to items available from the restaurant/café. In embodiments specific to diabetes therapy, a total number of carbohydrates contained in the selected items would be displayed along with optional suggestions of alternate menu items more in line with a user's therapy.

Figure 4:
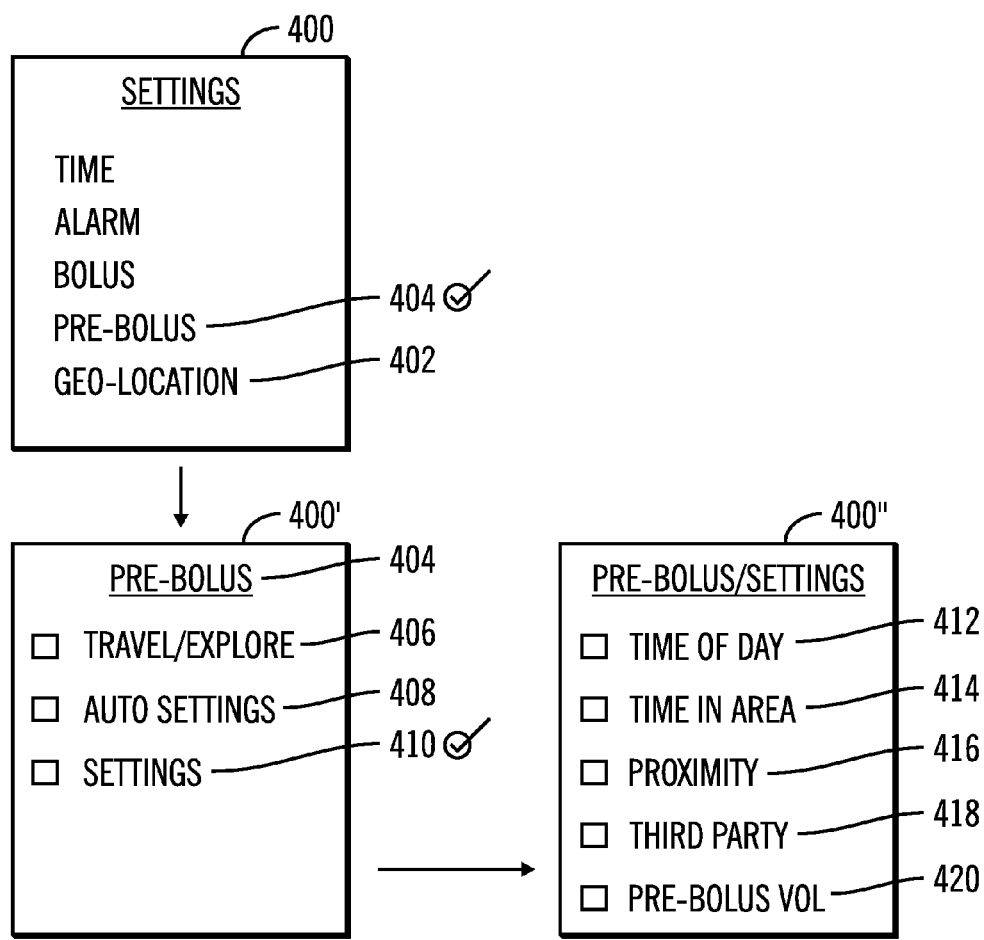
FIG. 4 includes exemplary screenshots to illustrate setting or programming pre-bolus features.

FIG. 4 includes exemplary screenshots to illustrate setting or programming pre-bolus features, in accordance with one embodiment of the present invention. Screen 400 is an exemplary display showing types of SETTINGS that can be configured on either the infusion pump or the controller. In one embodiment, without enabling GEO-LOCATION 402 a user would not be able to select PRE-BOLUS 404. In other embodiments, PRE-BOLUS 404 can still be configured without enabling or completely configuring GEO-LOCATION 402. The checkmark within a circle next to 404 indicates the selection of PRE-BOLUS 404 resulting in screen 400'.

Screen 400' is one embodiment of PRE-BOLUS 404 settings that are configurable by a user. Travel or explorer mode can be enabled by selecting the box next to TRAVEL/EXPLORER 406. Similarly, enabling automatic canceling or automatic delivery of a pre-bolus can be configured by selecting AUTO SETTINGS 408. In this exemplary embodiment, other settings for the pre-bolus can be set by selecting SETTINGS 410.

Screen 400" is an exemplary screen that is displayed after the checkmark next to 410 selects SETTINGS 410. On screen 400" a user can enable and configure various threshold settings such time of day thresholds by selecting TIME OF DAY 412. Configuration for TIME OF DAY 412 can include user specified times or data mining of previous bolus deliveries to determine times of day to enable pre-bolus suggestions. The time a user is within proximity of a known restaurant can be configured by selecting TIME IN AREA 414. Increasing the value for TIME IN AREA 414 requires a user to dwell within the proximity of a restaurant for a longer time before a pre-bolus suggestion is provided. By increasing the TIME IN AREA 414 the number of false notifications can be lowered, at the expense of delaying the delivery of the pre-bolus.

Figure 5:
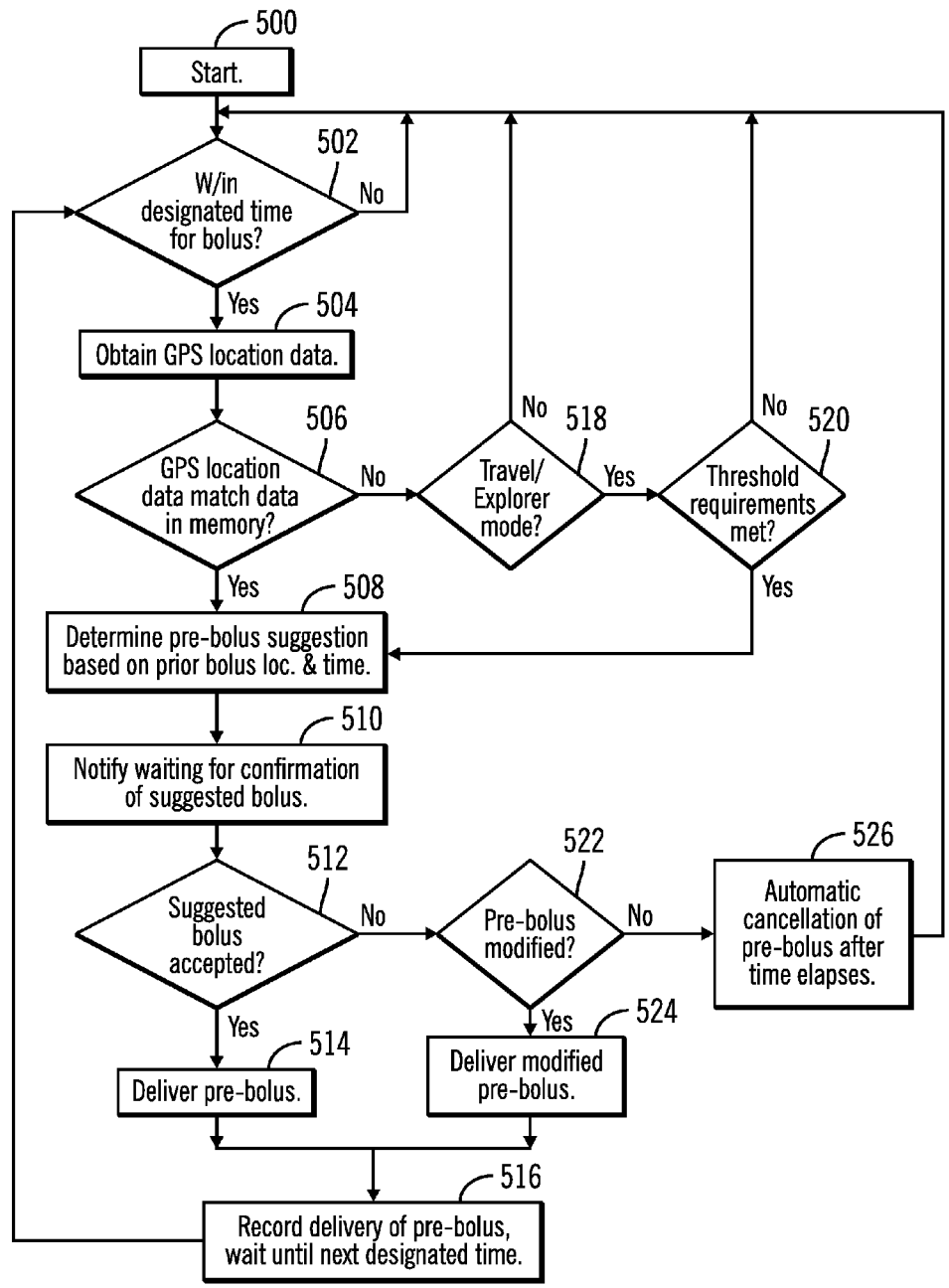
FIG. 5 is a flow chart illustrating exemplary operation of an infusion system with pre-bolus delivery.

The proximity thresholds to known GPS coordinates can be configured by selecting PROXIMITY 416. By increasing the value of PROXIMITY 416 a user may be further from the location of a known restaurant and still receive a pre-bolus notification. Configuration of third-party databases or applications is accomplished via THIRD PARTY 418. Selection of THIRD-PARTY 418 enables the selection of third-party applications such as YELP!, ZAGAT or GOOGLE MAPS. Once a third-party application is enabled further settings such as classification can be selected by the user. Pre-bolus volume suggestions can be configured via PRE-BOLUS VOL 420. In some embodiments selection of PRE-BOLUS VOL 420 allows a user to associate specific pre-bolus volumes for saved locations. In other embodiments, PRE-BOLUS VOL 420 allows configuration or enablement of automatic pre-bolus calculations based on prior bolus data. In still other embodiments pre-bolus volumes may be set to specific volumes depending on the time of day. FIG. 4 is intended to illustrate basic user interface options that enable configuration of pre-bolus settings. The particular options and settings and how they are depicted and discussed regarding screens 400, 400' and 400" should not be construed as exhaustive of configurable pre-bolus options. A pre-bolus can include other configurable options not shown in FIG. 4. Furthermore, the depictions on screens 400, 400' and 400" can be simplified via icons and other user interface enhancements FIG. 5 is a flow chart illustrating exemplary operation of an infusion system with pre-bolus delivery, in accordance with embodiments of the present invention. The flow chart is initiated with operation 500, START. Operation 502 determines if time of day thresholds are satisfied. Operation 504 obtains GPS location data for the infusion system if the time of day thresholds are satisfied. If the time of day thresholds are not satisfied, operation 502 is repeated. Operation 506 determines if the GPS location data matches location data stored in the memory of the infusion system. If the GPS location data is found in the memory, Operation 508 determines a pre-bolus suggestion based on prior bolus deliveries at the given location. In some embodiments the pre-bolus calculation performed in operation 508 further considers similar times for prior bolus deliveries. In other embodiments the pre-bolus volume is preset and a specified volume.

Operation 510 notifies the user that a pre-bolus suggestion requires confirmation or acceptance. Operation 512 determines if the suggested pre-bolus was accepted. If operation 512 was accepted operation 514 delivers the suggested pre-bolus. If operation 512 was not accepted, operation 522 determines if the pre-bolus was modified. Operation 524 delivers a modified pre-bolus if the pre-bolus was modified. If the pre-bolus was not modified in operation 522, operation 526 automatically cancels the pre-bolus after a specified time elapses. In other embodiments, a user can configure the infusion system to automatically deliver the suggested pre-bolus after a specified time elapses. Regardless of whether the pre-bolus is automatically canceled or delivered, after operation 526 the flow chart returns to operation 502. The flow chart similarly returns to operation 502 after operation 516 which follows either operation 514 or operation 524. Operation 516 records the time, volume and geo-tags the delivery of the pre-bolus in the memory of the infusion system.

If operation 506 determines that the GPS coordinates are not found in the infusion system memory or a third-party database, operation 518 determines if the travel/explorer mode for the infusion system is enabled. If the travel/explorer mode is not enabled the flow chart returns to operation 502. However, if the travel/explorer mode is enabled, operation 520 determines if the user defined thresholds are satisfied. While one embodiment has operation 520 following operation 518, in other embodiments, operation 520 is also found after operation 506 and before operation 508. In both embodiments, examples of user defined threshold includes, but are not limited to the time a user is within proximity of a known restaurant, the proximity a user must be to a restaurant, and any filters based on third-party data. The specific examples for user defined thresholds are intended to be exemplary and should not be construed as exhaustive. Additional thresholds can be utilized to reduce the number of false notifications and thereby improve the quality of the pre-bolus delivery system.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medical therapy system to deliver a pre-bolus volume of medicant, the medical therapy system comprising:
   an infusion pump having a case, the case containing a processor, memory, a drive mechanism, a reservoir, and communication hardware;
   the infusion pump further including a global positioning system (GPS) receiver to determine GPS coordinates of the infusion pump, the GPS receiver being coupled to the processor, the processor executing stored program instructions to provide notification for confirmation to deliver a pre-bolus volume from the reservoir when the GPS coordinates of the infusion pump are within a specified proximity of GPS coordinates of a known location.

2. The medical therapy system as defined in claim 1, wherein the known location is stored in the memory of the infusion system.

3. The medical therapy system as defined in claim 2, wherein known locations are created by recording the GPS coordinates, time and bolus volume for any bolus delivery by the infusion pump.

4. The medical therapy system as defined in claim 2, wherein a user inputs a known location into the memory of the infusion system.

5. The medical therapy system as defined in claim 1, wherein the known location is accessed via a third-party database.

6. The medical therapy system as defined in claim 1, wherein a threshold value is required before requesting confirmation of delivery of a pre-bolus volume.

7. The medical therapy system as defined in claim 6, wherein the threshold value is time of day.

8. The medical therapy system as defined in claim 7, wherein the time of day threshold is user configurable with a plurality of values.

9. The medical therapy system as defined in claim 8, wherein the time of day threshold values are automatically determined by repetition of times of previous bolus deliveries.

10. The medical therapy system as defined in claim 6, wherein the threshold value is a number of restaurants within a proximity of the GPS coordinates of the infusion pump.

11. The medical therapy system as defined in claim 10, wherein the proximity of the GPS coordinates of the infusion pump is user configurable.

12. The medical therapy system as defined in claim 11, wherein the number of restaurants is reported by a third party application, the third party application providing classifications for the number of restaurants.

13. The medical therapy system as defined in claim 12, wherein user configurable filters based on the provided classifications reduce the number of restaurants to a preferred selection of restaurants.

14. The medical therapy system as defined in claim 1, wherein the pre-bolus volume is determined from previous bolus deliveries.

15. The medical therapy system as defined in claim 14, wherein the previous bolus deliveries used to determine the pre-bolus volume are selected from previous bolus deliveries performed at substantially a same time and within close proximity to similar GPS coordinates.

16. The medical therapy system as defined in claim 1, wherein if confirmation to deliver the pre-bolus is not received in a specified period of time the pre-bolus is automatically canceled, the specified period of time being configurable.

17. The medical therapy system as defined in claim 1, wherein if confirmation to deliver the pre-bolus is not received in a specified period of time the pre-bolus is automatically delivered, the specified period of time being configurable.

18. The medical therapy system as defined in claim 1, wherein confirmation to deliver the pre-bolus is received via voice recognition.

19. The medical therapy system as defined in claim 1, further including an option to modify the pre-bolus volume before confirming delivery.

20. The medical therapy system as defined in claim 1, furthering including an option to delay the delivery of the pre-bolus by a user specified period of time.

* * * * *